United States Patent [19]

Neri et al.

[11] Patent Number: 5,264,604

[45] Date of Patent: Nov. 23, 1993

[54] OXAMIDIC STABILIZERS

[75] Inventors: Carlo Neri; Luciano Pallini, both of San Donato Milanese; Daniele Fabbri, Riccione, all of Italy

[73] Assignee: Enichem Synthesis S.p.A., Palermo, Italy

[21] Appl. No.: 3,631

[22] Filed: Jan. 13, 1993

[30] Foreign Application Priority Data

Jan. 14, 1992 [IT] Italy .................. MI92A000055

[51] Int. Cl.$^5$ ................ C07F 7/08; C07F 7/10
[52] U.S. Cl. ..................... 556/419; 524/188
[58] Field of Search ............ 556/419; 524/188

[56] References Cited

U.S. PATENT DOCUMENTS 5,049,689  9/1991  Peter et al. ............... 556/419 X

FOREIGN PATENT DOCUMENTS 338386 10/1989 European Pat. Off. .
461071 12/1991 European Pat. Off. .
1114640 10/1961 Fed. Rep. of Germany .

OTHER PUBLICATIONS

Albarino, R. V. et al. Retention of Thermal Antioxidants in Polyethylene by Silane Coupling Agents III. Copper Deactivation J. Appl. Polym. Sci., 19, No. 10, pp. 2667-2682 (1975).

Primary Examiner—Paul F. Shaver
Attorney, Agent, or Firm—Shea & Gould

[57] ABSTRACT

Oxamidic stabilizers containing organofunctional groups of silicon, capable of producing polymeric structures or of chemically binding themselves to a solid support.

9 Claims, No Drawings

OXAMIDIC STABILIZERS

The present invention relates to the stabilization of organic polymers.

In particular, it relates to a new group of siloxanic stabilizing additives containing oxamidic groups in the molecule, the procedure for the preparation of said stabilizing compounds and the polymeric compositions stabilized.

It is well known that organic polymers are subject to thermo-oxidative degradation. It is also known that the degradative process is accelerated by the presence of metals or metallic compounds.

Very often the polymers come in contact with metals, and this occurs both in the procedures for their preparation and while they are being used. This is the case for example, in the use of thermoplastic polymers, and particularly polyolefins, as insulating material for copper wires and cables.

To overcome the above degradation phenomena, stabilizing compounds known as metal deactivators such as, for example, the amides of oxalic acid, are generally introduced into the polymer.

In addition to their stabilizing properties, these compounds must have a set of other characteristics, including a high resistance to extraction.

This property is important especially when the use of the end-products involves contact with particular substances or solvents capable of extracting the stabilizing additive, or contact with food in which case absolute non-migration of the additive towards the surface must be guaranteed, or in the stabilization of polymeric mixtures or copolymers, or finally when composite products must be produced composed of multilayers organic polymers or of polymer and inorganic support. In the latter case, in fact, the migration of the additive almost always causes a detachment of the various layers, a loss in the mechanical characteristics of the end-product and a more rapid degradation of the organic material.

A new group of stabilizing compounds has now been found, which are capable of producing polymeric structures or of binding themselves to a solid support, and thus remaining over a period of time inside the polymer in which they have been incorporated.

The present invention therefore relates to organofunctional compounds of silicon having formula (I):

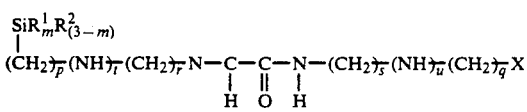

wherein $R^1$ is a linear or branched alkyl containing from 1 to 10 carbon atoms, or a phenyl, $R^2$ is equal to $OR^1$ or Cl, X is H or $-SiR^1_m R^2_{(3-m)}$, m is 0, or 1 or 2, p and q, the same or different, are integers between 1 and 10, r and s, the same or different, are integers between 0 and 10, t and u, the same or different, are 0 or 1.

Among the compounds having formula (I), those belonging to the following groups are preferred:

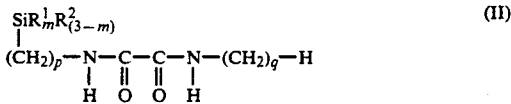

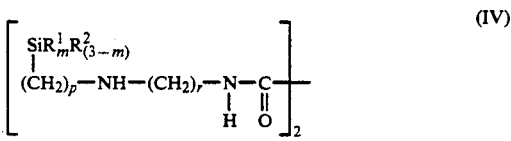

wherein $R^1$, $R^2$, m, p, q, r, have the previously defined meaning.

Compounds which are particularly preferred are those where $R^1$ is a methyl or an ethyl, and $R^2$ is a methoxylic or ethoxylic radical.

The present invention also relates to polysiloxanes obtained by the polymerization of compounds having formula (I).

Polysiloxanes are obtained from the polymerization reaction, having more or less complex structures, partially branched or even cross-linked.

When the polymerization reaction is specifically carried out on compounds belonging to the group having formula (II) wherein m=1, polysiloxanes having a linear or cyclic structure are obtained, which can be represented by the following formula (V):

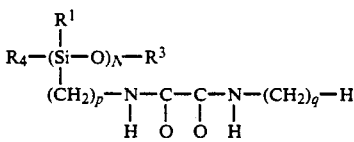

where $R^3$ is equal to H or $R^1$, $R^4$ is equal to OH or $R^4$, $R^3$ and $R^4$ optionally being able to jointly form a direct bond thus producing a cyclic structure, n is an integer between 2 and 10, $R^1$, $R^2$, p, q, have the meaning defined above.

The compounds having formula (I) wherein X is equal to $SiR^1_m R^2_{(3-m)}$ are prepared by the reaction of diethyloxalate with compounds having formula (VI):

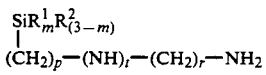

where $R^1$, $R^2$, m, p, r, t have the meaning previously defined.

To prepare the compounds having formula (I) wherein X is a hydrogen atom, an intermediate is prepared by the reaction of diethyloxalate with an amine having formula (VII):

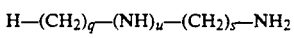

where q, u, s have the meaning previously defined. The product obtained is then reacted with a compound having formula (VI), where $R^1$, $R^2$, m, p, r, t, have the meaning previously defined.

The above reactions are carried out in the presence of an organic solvent selected from alcohols, ethers or hydrocarbons. Suitable solvents are, for example, toluene and n-hexane.

The reaction temperature ranges from 10° to 150° C. The reaction is preferably carried out at room temperature.

When the reaction has finished the product is recovered after the volatile products have been removed by distillation.

The polymerization reaction of the compounds having formula (I) thus obtained consists of a first stage of hydrolysis in an aqueous solution, in the presence of catalysts such as, for example, alkaline hydroxides, mineral acids, organic acids dibutyltindilaurate, zinc octanoate. The temperature ranges from 10° to 100° C.

Treatment is then carried out at reduced pressure, at temperatures ranging from 60° to 150° C., for a period of 2 to 12 hours.

The organic polymers which can be stabilized with the compounds of the present invention include polyolefins, such as LDPE, LLDPE, HDPE, XLPE, polypropylene, their copolymers, terpolymers EPDM, ABS and synthetic rubbers.

The stabilizers of the present invention are added to the polymer to be stabilized in the compounding phase. More generally, they are added in the final phase of the synthesis process of the polymer or in the production phase of the end products. The latter is the more commonly used technique in practice, in that it allows an addition level which conforms to the characteristics of the end product.

The stabilizers of the present invention can be used in combination with one or more additional additives selected, for example, from antioxidants, heat and light stabilizers, basic co-stabilizers and nucleating agents.

In particular, additives based on sterically hindered amines can be used, such as those corresponding to the trade-names Uvasil 299, Tinuvin 770, Tinuvin 662, Chimassorb 944, or antioxidants of the sterically hindered phenyl group such as Anox 20, Anox PP18, BHT, or phosphites and/or phosphonites such as Ultranox 626, Weston 618, Alkanox 240, Sandostab PEPQ, or finally organic compounds containing sulphur such as distearyl thiodipropionate and dilauryl thiodipropionate.

The quantity of stabilizing additive normally used according to the present invention varies from 0.05% to 1% by weight of the polymer to be stabilized, and preferably 0.1-0.5%.

The following examples provide a better illustration of the present invention but do not limit it in any way.

EXAMPLE 1

Preparation of the intermediate (A) having the formula:

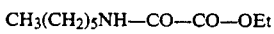

CH₃(CH₂)₅NH—CO—CO—OEt 29.20 g (0.20 moles) of diethyloxalate and 50 ml of n-hexane are charged into a 100 ml flask, equipped with a magnetic stirrer and drip funnel. 20.24 g (0.20 moles) of hexylamine are then added dropwise and the mixture is left to react for two hours at room temperature.

It is then cooled to 0° C. to precipitate the N,N-diethyloxamide which is filtered away. 28.0 g of the intermediate (A) are obtained from the solution in hexane by distillation at reduced pressure, with a 70% yield and 98% purity determined by gaschromatography.

Characterization:
PMR spectrum in p.p.m.: 7.1s (1H); 4.25q (2H); 3.26q (2H); 1.49m (2H); 1.28t, 1.21m (9H); 0.80t (3H).
Infrared spectrum, main absorption bands (cm⁻¹): 3320, 1740–1700, 1535, 1220.

EXAMPLE 2

Preparation of the compound having the formula:

(EtO)₃Si(CH₂)₃NH—CO—CO—NH(CH₂)₅CH₃

10.05 g (0.050 moles) of intermediate (A) and 11.07 g (0.050 moles) of γ-aminopropyl-triethoxysilane dissolved in 30 ml of n-hexane are charged into a 100 ml flask, equipped with a magnetic stirrer and drip-funnel.

The mixture is left to react for two hours at room temperature, and the volatile products are then removed by distillation. 17.20 g of a white solid are obtained which on gaschromatographic analysis proves to be the desired compound with a 94% purity. The yield is 91%.

Characterization:
Melting point: 46° C.
PMR spectrum in p.p.m.: 7.6–7.5m (2H); 3.75q (6H); 3.24m (4H); 1.62m, 1.50m (4H); 1.19m, 1.16t (15H); 0.82t (3H); 0.57m (2H).
Infra-red spectrum, main absorption bands (cm⁻¹): 3310, 1670, 1530, 1100, 960, 780.

EXAMPLE 3

Preparation of the compound having the formula:

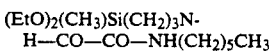

(EtO)₂(CH₃)Si(CH₂)₃NH—CO—CO—NH(CH₂)₅CH₃

Using the same procedure described in the previous example, 17.70 g (0.088 moles) of intermediate (A) are reacted with 16.84 g (0.088 moles) of 3-(diethoxymethylsilyl) propylamine dissolved in 30 ml of n-hexane. 30.30 g of a white solid are obtained which on gaschromatographic analysis proves to be the desired compound with a 95% purity. The yield is 99%.

Characterization
Melting point: 34° C.
PMR spectrum in p.p.m.: 7.65m (2H); 3.68q (4H); 3.22qd (4H); 1.5m (4H); 1.20m, 1.13t (12H); 0.80t (3H); 0.54m (2H); 0.036s (3H).
Infra-red spectrum, main absorption bands (cm⁻¹): 3320, 1670, 1525, 1110, 1085, 960.

EXAMPLE 4

Preparation of the compound having the formula:

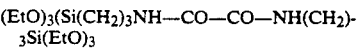

(EtO)₃Si(CH₂)₃NH—CO—CO—NH(CH₂)₃Si(EtO)₃

15.10 g (0.068 moles) of γ-aminopropyltriethoxysilane and 60 ml of toluene are charged into a 100 ml flask, equipped with a magnetic stirrer and drip-funnel. 4.94 g (0.034 moles) of diethyloxalate are added dropwise to the solution, and the mixture is left to react for an hour at room temperature. The volatile products are removed by distillation and 16.46 g of a solid having a low melting point are obtained which on gaschromatographic analysis proves to be the desired compound with a 95% purity. The yield is 98%.

Characterization

PMR spectrum in p.p.m.: 7.55t (1H); 3.77q (6H); 3.27q (2H); 1.63m (2H); 1.17t (9H); 0.59m (2H).

Infra-red spectrum, main absorption bands (cm$^{-1}$): 3310, 1670, 1515, 1105, 1085, 960, 780.

EXAMPLE 5

Preparation of the compound having the formula:

$$[(CH_3O)_3Si(CH_2)_3NH(CH_2)_2NH-CO-]_2$$

5.11 g (0.035 moles) of diethyloxalate and 15.60 g (0.070 moles) of N-[3-(trimethoxysilyl)propyl] ethylene diamine dissolved in 60 ml of n-hexane are charged into a 100 ml flask, equipped with a magnetic stirrer and drip-funnel.

The mixture is left to react for two hours at room temperature. The suspension which is formed is poured into a separating funnel; the denser phase is recovered, washed with n-hexane and treated under vacuum.

15.60 g of a colourless liquid are obtained which on gaschromatographic analysis proves to be the desired compound with an 87% purity. The yield is 89%.

Characterization

PMR spectrum in p.p.m.: 7.8t (1H); 3.48s (9H); 3.32q (2H); 2.71t (2H); 2.53t (2H); 1.46m (2H); 1.4s(1H); 0.57m (2H).

Infra-red spectrum, main absorption bands (cm$^{-1}$): 3320, 1670, 1520, 1195, 1085, 820.

EXAMPLE 6

Polymerization of the compound of Example 3

5.41 g of the compound of Example 3, 20 ml of ethanol, 5.0 ml of water and 33 mg of NaOH are charged into a 100 ml flask, equipped with a magnetic stirrer, thermometer and cooler. The solution is heated to 80° C. and left to react for three hours; the ethanol is then removed by distillation, 10 ml of water are added and the solution is left for an hour at 80° C.

A precipitate is formed which is filtered, washed with water and dried under vacuum at 120° C. 3.50 g of a white solid are thus obtained. The yield is 83%.

Characterization

PMR spectrum in p.p.m.: 8.1 (2H); 3.25 (4H); 1.51 (4H); 1.23 (6H); 0.82 (3H); 0.49 (2H); 0.013 (3H).

Infra-red spectrum, main absorption bands (cm$^{-1}$): 3310, 1655, 1530, 1075.

EXAMPLE 7

Polymerization of the compound of Example 4

Using the same procedure described in the previous example, 15.1 g of the compound of Example 4, 15 ml of water and 50 mg of NaOH are reacted at 90° C. for 3 hours. The solution is then treated under vacuum at 120° C. for a further 3 hours.

10.0 g of a white solid are obtained, which is insoluble in common solvents.

EXAMPLE 8

Preparation of polypropylene stabilized with the compounds of the invention

Using the stabilizing compounds prepared as described in Examples 2-7, mixtures are prepared with commercial polypropylene of the type MOPLEN FLF 20 at 0.2% by weight of stabilizer. Said mixtures also contain 1% by weight of copper powder.

Each of the mixtures is extruded in a Brabender-type laboratory extruder with a screw rate of 6 rpm and with the following temperature profile from the head to the bottom zones: 175°-200°-210°-220° C.

The samples thus extruded are cut into pellets and pressed for 3 minutes at 200° C., to obtain slabs having a thickness of 0.5 mm.

Slabs of polypropylene as such (comparison A) and of polypropylene containing 1% of copper powder (comparison B) are similarly prepared.

The slabs thus obtained were subjected to thermal treatment in a hot air-circulation oven at 135° C.

To observe the degradation process in the test samples the embrittlement times (E.T.) are noted. The results are shown in Table 1.

EXAMPLE 9

Preparation of HDPE stabilized with the compounds of the invention

Using the same procedure described in the previous example, slabs of HDPE containing 0.2% by weight of the monomeric stabilizing compound of Example 3 and of the polymeric compound of Example 6 are prepared.

A set of slabs thus prepared are extracted in soxhlet for 7 hours with methylene chloride; in the same way a second set of slabs is extracted with heptane.

The quantity of stabilizing additive in the slabs is evaluated by IR spectroscopy, calculating the absorbance variation at 1660 cm$^{-1}$.

The extraction resistance (ER) of the additive is expressed as:

$$ER = A/A_0 \times 100$$

where $A_0$ and $A$ are the absorbance values before and after the extraction treatment respectively.

The results, shown in Table II, show how the polymeric stabilizer is considerably more resistant to extraction than the monomeric stabilizer.

TABLE I

| Additive | E.T. |
| --- | --- |
| Example 2 | 16 |
| Example 3 | 15 |
| Example 4 | 15 |
| Example 5 | 10 |
| Example 6 | 25 |
| Example 7 | 14 |
| Comparison A | 20 |
| Comparison B | 5 |

TABLE II

| | RE | |
| --- | --- | --- |
| Additive | Methylene chloride | Heptane |
| Example 3 | <5% | <5% |
| Example 6 | 80% | 75% |

We claim:

1. Organofunctional compounds of silicon having formula (I):

$$SiR^1{}_mR^2{}_{(3-m)}$$
$$(CH_2)_p-(NH)_r-(CH_2)_t-N-C-C-N-(CH_2)_s-(NH)_u-(CH_2)_q-X$$
$$\phantom{(CH_2)_p-(NH)_r-(CH_2)_t-N-}\underset{H}{|}\ \underset{O}{\|}\ \underset{O}{\|}\ \underset{H}{|}$$

wherein $R^1$ is a linear or branched alkyl containing from 1 to 10 carbon atoms, or a phenyl, $R^2$ is $OR^1$ or Cl, X is H or $-SiR^1_m R^2_{(3-m)}$, m is 0, 1 or 2, p and q, the same or different, are integers between 1 and 10, r and s, the same or different, are integers between 0 and 10, t and u, the same or different, are 0 or 1.

2. Organofunctional compounds of silicon having formula (II):

$$\begin{array}{c} SiR^1_m R^2_{(3-m)} \\ | \\ (CH_2)_p-N-C-C-N-(CH_2)_q-H \\ \phantom{(CH_2)_p-}| \phantom{-}\| \phantom{-}\| \phantom{-}| \\ \phantom{(CH_2)_p-}H \phantom{-}O \phantom{-}O \phantom{-}H \end{array}$$

wherein $R^1$ is a linear or branched alkyl containing from 1 to 10 carbon atoms, or a phenyl, $R^2$ is $OR^1$ or Cl, m is 0, 1, or 2, and, p and q, the same or different, is an integer between 1 and 10.

3. Organofunctional compounds of silicon having formula (III):

$$\left[ \begin{array}{c} SiR^1_m R^2_{(3-m)} \\ | \\ (CH_2)_p-N-C- \\ \phantom{(CH_2)_p-}| \phantom{-}\| \\ \phantom{(CH_2)_p-}H \phantom{-}O \end{array} \right]_2$$

wherein $R^1$ is a linear or branched alkyl containing from 1 to 10 carbon atoms, or a phenyl, $R^2$ is $OR^1$ or Cl, X is H or $-SiR^1_m R^2_{(3-m)}$, m is 0, 1, or 2, p and q, the same or different, are integers between 1 and 10, and, r is an integer between 0 and 10.

4. Organofunctional compounds of silicon having formula (IV):

$$\left[ \begin{array}{c} SiR^1_m R^2_{(3-m)} \\ | \\ (CH_2)_p-NH-(CH_2)_r-N-C- \\ \phantom{(CH_2)_p-NH-(CH_2)_r-}| \phantom{-}\| \\ \phantom{(CH_2)_p-NH-(CH_2)_r-}H \phantom{-}O \end{array} \right]_2$$

wherein $R^1$ is a linear or branched alkyl containing from 1 to 10 carbon atoms, or a phenyl, $R^2$ is $OR^1$ or Cl, X is H or $-SiR^1_m R^2_{(3-m)}$, m is 0, 1, or 2, p and q, the same or different, are integers between 1 and 10, and, r is an integer between 0 and 10.

5. Organofunctional compounds of silicon according to claims 1, 2, 3, or 4 where $R^1$ is a methyl group or an ethyl group.

6. Organofunctional compounds according to claims 1, 2, 3, or 4 where $R^2$ is a methoxy group or an ethoxy group.

7. Polysiloxanes obtained by the polymerization of the compounds according to claims 1, 2, 3, or 4.

8. Method for the stabilization of an organic polymer, which comprises incorporating into said polymer a stabilizing amount of a compound according to claims 1, 2, 3, or 4.

9. Polymeric compositions comprising an organic polymer and a stabilizing amount of a compound according to claims 1, 2, 3, or 4.

* * * * *